US00PP16687P3

(12) United States Plant Patent
Miyazaki

(10) Patent No.: US PP16,687 P3
(45) Date of Patent: Jun. 20, 2006

(54) ***SENECIO* PLANT NAMED 'SUNSENEBABU'**

(50) Latin Name: ***Senecio cruentus*×*Senecio heritieri***
Varietal Denomination: Sunsenebabu

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 49 days.

(21) Appl. No.: 10/814,612

(22) Filed: Mar. 30, 2004

(65) Prior Publication Data

US 2005/0223449 P1 Oct. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,104 P2 9/2001 Miyazaki

FOREIGN PATENT DOCUMENTS

JP PBR 10504 9/2002

OTHER PUBLICATIONS

Explanation of Publications of Japanese PBR Registration and family documents thereof.

Suntory Flowers Ltd., "Flower & Green, Autumn to Winter catalog 2003" Published 2003 (Explanation for IDS Document).

Moerheim New Plant bv, "Suntory Collection 2004" Published 2003 (Explanation for IDS Document).

Sakata Seed Co., "Sakata Seed, Catalog for Gardening Farm, Autumn '94 to Spring '95, Sakata's flowering plants, nursery stocks, and bulbs, No. 70" Published 1994 (Explanation for IDS Document).

The Royal Horticultural Society, "The Plant Finder, 1994/95 Edition" Published 1994 (Explanation for IDS Document).

*Primary Examiner*—Kent Bell
*Assistant Examiner*—Louanne Krawczewicz Myers
(74) *Attorney, Agent, or Firm*—Christie, Parker and Hale, LLP

(57) ABSTRACT

Disclosed herein is a new variety of *Senecio* plant having a semi-dwarf, obconical shape with abundant branching and small leaves. The capitula are single and small, the ray florets have a vivid violet color and the disc floret color is brilliant violet. The blooming time is early and flowering duration is longer than *Senecio cruentus*. 'Sunsenebabu' has low fertility.

2 Drawing Sheets

Botanical classification: *Senecio cruentus*×*Senecio heritieri*.
Varietal denomination: 'Sunsenebabu'.

BACKGROUND OF THE VARIETY

The present invention relates to a new variety of *Senecio* plant, which originated from the crossing of the cultivar 'Extra Blue' (unpatented) as the female parent with a variety of *Senecio heritieri* as the male parent.

There are many varieties in *Senecio L.* and *Senecio cruentus,* well known as *Senecio,* cultivated in the world. There are many cultivated varieties with capitula of a single color of white, pink red, blue or violet. Some varieties have marginal variegation with off color parts.

The female parent 'Extra Blue' used in the crossing that produced 'Sunsenebabu' is a cultivar of *Senecio cruentus*. It is early flowering variety having dwarf and mounding shape with large leaves. It has small single capitula, the ray florets having a vivid purple color. The seed of 'Extra Blue' is commercially available.

The male parent *Senecio heritieri* used in the crossing that produced 'Sunsenebabu' is a cultivar having a high and dome-shaped growth habit with abundant branching and small leaves. It has small single capitula, the ray florets having strong purple with vague white center coloration.

*Senecio heritieri,* introduced from nurseries in England, has no variety name and, to Applicant's knowledge, is neither patented nor sold in the United States.

In January 1996, crossing of 'Extra Blue' as the female parent and *Senecio heritieri* as the male parent was conducted at Hakushu-cho, Kitakoma-gun, Yamanashi-ken, Japan. The seedlings obtained from that crossing were grown in pots in glasshouses and evaluated from July 1996. One seedling was selected in view of its growth habit, flower color and flowering time in December 1996. That seedling was propagated by cutting and grown in pots. A trial was carred out in pots from July 1999, at Hakushu-cho, Kitakoma-gun, Yamanashi-ken, Japan. The botanical characteristics of that plant were then examined, using similar varieties 'Sunsenebu' (U.S. Plant Pat. No. 12,104) and 'Miss Yokohama' (unpatented) for comparison. As a result, it was concluded that this *Senecio* plant is distinguishable from any other variety, whose existence is known to us, and is uniform and stable in its characteristics. The new variety of *Senecio* plant was named 'Sunsenebabu'.

The new variety was first asexually reproduced by cuttings in Hakushu-cho, Kitakoma-gun, Jamanashi, Japan.

In the following description, the color-coding is in accordance with The Horticultural Colour Chart of The Royal Horticultural Society, London, England (R.H.S.).

SUMMARY OF THE VARIETY

This new variety is unlike any *Senecio* commercially available known to the inventor as evidenced by the following unique combinations of characteristics.

1. Semi-dwarf, obconical plant shape having abundant branching with small leaves.
2. The capitula are single and small. The ray floret color is vivid violet (near R.H.S. 94A). The disc floret color is brilliant violet (near R.H.S. 68D).
3. Blooming time is early, and flowering duration is long.
4. Low fertility.

The new variety 'Sunsenebabu' differs from the similar variety 'Sunsenebu' in the following points.

1. The plant size of 'Sunsenebabu' is smaller than that of 'Sunsenebu'.
2. The capitulum diameter of 'Sunsenebabu' is smaller than that of 'Sunsenebu'.
3. The disc floret color of 'Sunsenebabu' is brilliant violet (near R.H.S. 89D), while that of 'Sunsenebu' is deep violet (near R.H.S. 93A).
4. The peduncle length of 'Sunsenebabu' is shorter than that of 'Sunsenebu'.
5. The blooming time of 'Sunsenebabu' is earlier than that of 'Sunsenebu'.

The new variety 'Sunsenebabu' differs from the similar variety 'Miss Yokohama' in the following points.

1. The plant height of 'Sunsenebabu' is higher than that of 'Miss Yokohama'.
2. The number of the branches of 'Sunsenebabu' is more than that of 'Miss Yokohama'.
3. The leaf of 'Sunsenebabu' is smaller than that of 'Miss Yokohama'.
4. The disc floret color of 'Sunsenebabu' is brilliant violet (near R.H.S. 89D) while that of 'Miss Yokohama' is vivid violet (near R.H.S. 96A).
5. The blooming time of 'Sunsenebabu' is earlier than that of 'Miss Yokohama'.
6. The flowering duration of 'Sunsenebabu' is longer than that of 'Miss Yokohama'.

This new variety of *Senecio* Plant 'Sunsenebabu' was asexually reproduced by the use of cuttings at Hakushu-cho, Kitakoma-gun, Yamanashi-ken, Japan, and homogeneity and stability thereof were confirmed. The instant plant retains its distinctive characteristics and reproduces true to type in successive generations.

BRIEF DESCRIPTION OF THE PHOTOGRAPHS

The depicted plants had been reproduced by the use of cuttings and were photographed during January 2003 while growing outdoors in 12 cm pots at an age of approximately 5 months at Yokaichi-shi, Shiga-ken, Japan.

DESCRIPTION OF THE VARIETY

Figure 1:
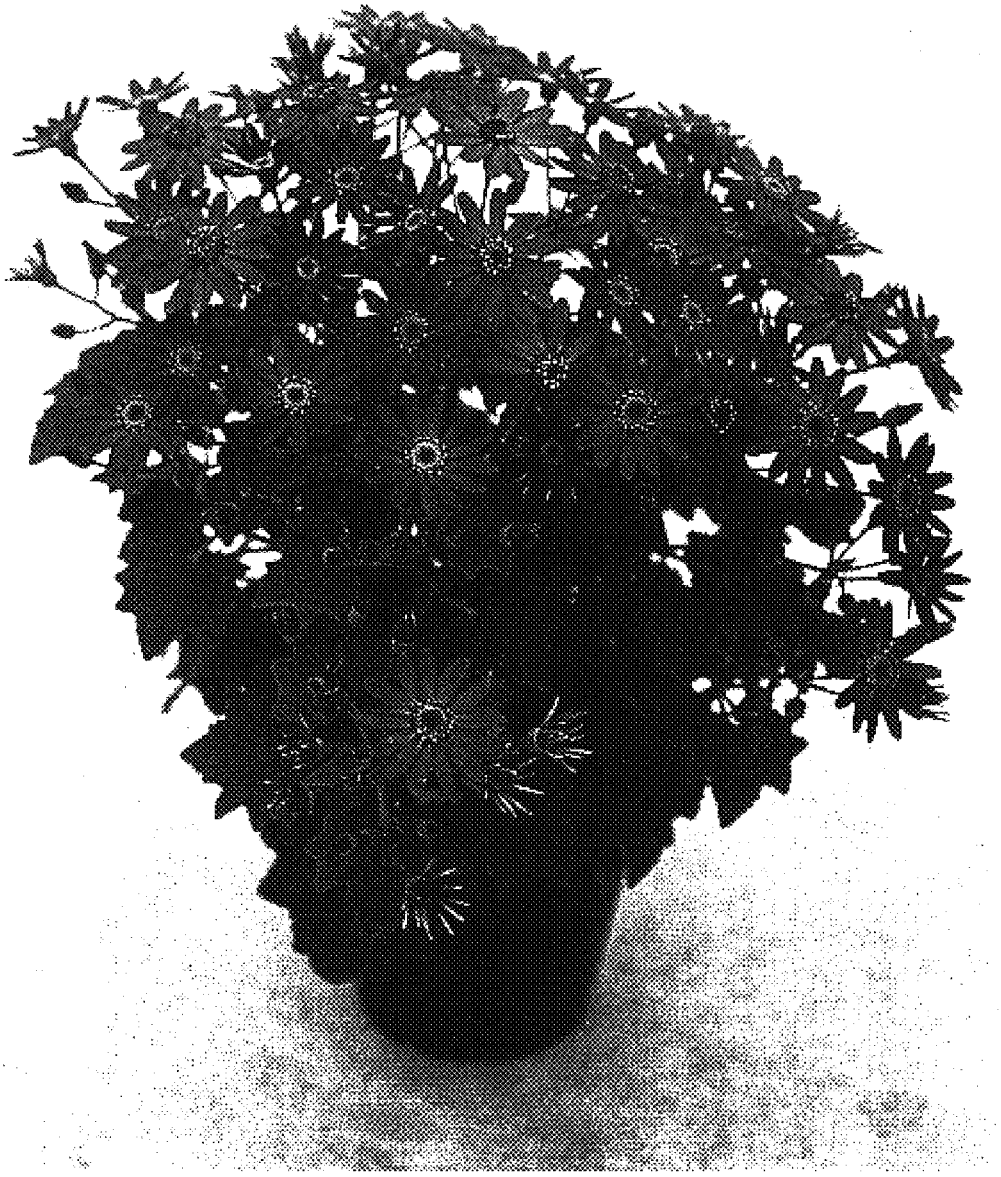
FIG. 1 illustrates a typical plant of the new variety of *Senecio* plant 'Sunsenebabu' growing in a pot.
Figure 2:
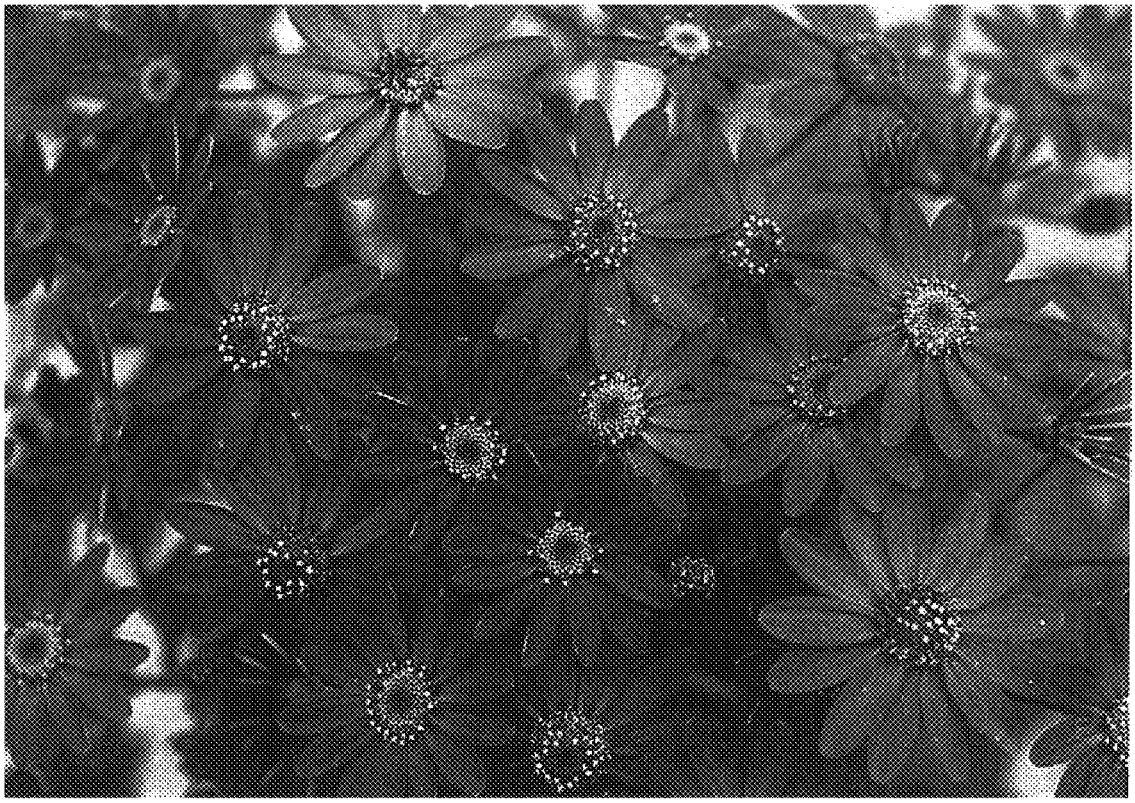
FIG. 2 illustrates a close-up view of typical capitula of the new variety of *Senecio* plant 'Sunsenebabu'.

The botanical characteristics of the new and distinct variety of *Senecio* plant named 'Sunsenebabu' are as follows when observed during January at Yokaichi-shi, Shiga-ken, Japan, at an age of approximately 5 months.

Plant:
- *Growth habit.*—Semi-dwarf, obconical.
- *Height.*—Approximately 27 cm.
- *Width.*—Approximately 18 cm.

Stem:
- *Length.*—Approximately 16 cm.
- *Thickness.*—Approximately 3.5 mm.
- *Color.*—Near R.H.S. 139C.
- *Anthocyanin coloration.*—Present in parts of the stem, e.g., can be seen at the part of peduncle (near R.H.S. N79B).
- *Number of branches.*—Abundant.
- *Type of primary lateral shoot.*—Branch from every node.
- *Pubescence.*—Dense.
- *Length of internode.*—Approximately 1.5 cm.

Leaf:
- *Whole shape.*—Cordate.
- *Leaf margin.*—Dentate, weakly undulated.
- *Apex shape.*—Obtuse.
- *Base shape.*—Cordate.
- *Length.*—Approximately 6.8 cm.
- *Width.*—Approximately 7.8 cm.
- *Diameter of petiole.*—Approximately 3.4 mm.
- *Length of petiole.*—Approximately 5.5 cm.
- *Color of petiole.*—Near R.H.S. 138B.
- *Color of upper surface.*—Near R.H.S. 146A.
- *Color of lower surface.*—Near R.H.S. 191B.
- *Anthocyanin coloration of lower surface.*—Absent.
- *Pubescence of upper surface.*—Moderate.
- *Pubescence of lower surface.*—Dense.
- *Pattern of venation.*—Reticulate.
- *Color of venation.*—Near R.H.S. 138B.
- *Stipule.*—Absent.

Inflorescence cluster (gathering of corymbs):
- *Shape of inflorescence cluster.*—Flat.
- *Diameter of inflorescence cluster.*—Approximately 31 cm.
- *Height of inflorescence cluster.*—Approximately 19 cm.

Capitulum:
- *Transected shape of capitulum.*—Flat.
- *Diameter of capitulum.*—Approximately 4.4 cm.
- *Disc diameter.*—Approximately 1.1 cm.
- *Color of ray floret.*—Upper surface — Near R.H.S. 94A; Lower surface — near R.H.S. 90D.

Disc floret:
- *Shape.*—Tubular, trumpet shape.
- *Color.*—Both surfaces near R.H.S. N88A to N88C.
- *Length.*—Approximately 8.5 mm.
- *Diameter.*—Approximately 1.0 mm.
- *Margin.*—5 lobed, star shape.
- *Apex shape.*—Acute.
- *Base shape.*—Fused.
- *Marginal variegation.*—Absent.
- *Ray floret length.*—Approximately 1.8 cm.
- *Ray floret width.*—Approximately 0.6 cm.
- *Shape of ray floret.*—Oblong.
- *Lengthwise warp of ray floret.*—Flat.
- *Shape of ray floret tip.*—Obtuse.
- *Shape of ray floret base.*—Obtuse.
- *Margin of ray floret.*—Entire.
- *Texture.*—Velvety.
- *Number of ray florets.*—13 (single whorl).
- *Number of disc florets.*—Approximately 110.

*Diameter of pedicel.*—Approximately 1.1 mm.
*Length of pedicel.*—Approximately 4.1 cm.
*Number of capitula per plant.*—Approximately 80.
*Scent.*—Present.
*Bud.*—Hardiness — Tolerant to 0° C. However, the plant would be seriously damaged by frost, as other *Senecio* plants, at any temperature. Length — Approximately 5.5 mm. Diameter — Approximately 6.0 mm. Shape — Globose. Surface — Smooth. Color — Near R.H.S. 138A.

Involucre:
*Type.*—Bracts in a whorl, fused at the base, not recurred.
*Length of bracts* (*separated portion*).—Approximately 1.1 mm.
*Width of bracts* (*separated portion*).—Approximately 1.0 mm.
*Number of bracts per capitulum.*—Approximately 14.
*Margin of bracts.*—Entire.
*Apex shape of bracts.*—Acute.
*Color* (*both surfaces*).—Near R.H.S. 144B.
*Anthocyanin coloration* (*both surfaces*).—Absent.

Pistil:
*Color.*—Near R.H.S. 86B (strong purple).
*Number.*—1 per ray and disc floret.
*Type.*—Style branches truncate.

Stamen:
*Pollen.*—Moderate, color near R.H.S. 10A.
*Color.*—Near R.H.S. 86B (strong purple).
*Type.*—Synantherous. A disc floret has 5 connate anthers with separated filament. Ray floret has no stamen.
*Blooming time.*—Beginning of November to May. In Japan, plants start flowering about 5 months after planting rooted cuttings.
*Lastingness of an individual bloom on the plant.*—Approximately 2 weeks at around 15° C.

Hardiness:
*Cold.*—Good.
*Heat.*—Good.

Resistance:
*Disease.*—Good.
*Insect.*—Good.

The new variety and *Senecio cruentus* have similar resistance to powdery mildew, leaf spot, aphid, whitefly and thrips. The new variety, 'Sunsenebabu' is most suitable for flower potting.

It is claimed:

1. A new variety of *Senecio* plant named 'Sunsenebabu', substantially as herein illustrated and described.

* * * * *